United States Patent
Bhat et al.

(10) Patent No.: US 10,485,488 B2
(45) Date of Patent: Nov. 26, 2019

(54) EVENT DETECTION USING A VARIABLE THRESHOLD

(71) Applicant: Cardiac Pacemakers, Inc., St. Paul, MN (US)

(72) Inventors: Maya Bhat, Saint Paul, MN (US); Viktoria A. Averina, Shoreview, MN (US); Jonathan Walter Krueger, New Richmond, WI (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 239 days.

(21) Appl. No.: 15/190,511

(22) Filed: Jun. 23, 2016

(65) Prior Publication Data
US 2017/0027527 A1    Feb. 2, 2017

Related U.S. Application Data

(60) Provisional application No. 62/184,021, filed on Jun. 24, 2015.

(51) Int. Cl.
*A61B 5/042*    (2006.01)
*A61B 5/00*    (2006.01)
(Continued)

(52) U.S. Cl.
CPC .............. *A61B 5/742* (2013.01); *A61B 5/042* (2013.01); *A61B 5/4842* (2013.01); *A61B 5/7264* (2013.01); *A61B 5/7275* (2013.01); *A61B 5/7282* (2013.01); *A61B 5/746* (2013.01); *A61B 5/7445* (2013.01); *A61N 1/36585* (2013.01);
(Continued)

(58) Field of Classification Search
CPC ...... A61B 5/04015; A61B 5/0402; A61B 5/02
See application file for complete search history.

(56) References Cited

U.S. PATENT DOCUMENTS

| | | | |
|---|---|---|---|
| 7,979,130 B2 * | 7/2011 | Carlson | A61B 5/02405 600/544 |
| 2004/0249249 A1 * | 12/2004 | Lawson | A61B 5/02405 600/300 |

(Continued)

FOREIGN PATENT DOCUMENTS

| | | |
|---|---|---|
| AU | 2016282695 B2 | 2/2019 |
| CN | 102165306 A | 8/2011 |

(Continued)

OTHER PUBLICATIONS

"Australian Application Serial No. 2016282695, First Examination Report dated May 2, 2018", 3 pgs.
(Continued)

*Primary Examiner* — George R Evanisko
(74) *Attorney, Agent, or Firm* — Schwegman Lundberg & Woessner, P.A.

(57) ABSTRACT

Devices and methods for detecting an event using a variable threshold. A patient monitoring system can receive physiologic information and compare the information to an onset threshold. When the onset threshold is exceeded, the system shifts to a reset threshold that is different than the onset threshold. When the reset threshold is crossed, the system shifts back to the onset threshold.

20 Claims, 7 Drawing Sheets

(51) Int. Cl.
  *A61N 1/365* (2006.01)
  *A61N 1/39* (2006.01)
  *G16H 50/30* (2018.01)
  *G16H 50/20* (2018.01)
  *A61B 5/02* (2006.01)
  *A61B 5/11* (2006.01)
  *A61B 7/04* (2006.01)

(52) U.S. Cl.
  CPC ........... *A61N 1/3987* (2013.01); *G16H 50/20* (2018.01); *G16H 50/30* (2018.01); *A61B 5/02028* (2013.01); *A61B 5/1107* (2013.01); *A61B 5/6801* (2013.01); *A61B 5/743* (2013.01); *A61B 7/04* (2013.01)

(56) References Cited

U.S. PATENT DOCUMENTS

| | | |
|---|---|---|
| 2008/0228090 A1 | 9/2008 | Wariar et al. |
| 2009/0012416 A1 | 1/2009 | Belalcazar et al. |
| 2009/0043355 A1 | 2/2009 | Cazares et al. |
| 2010/0030292 A1 | 2/2010 | Sarkar et al. |
| 2010/0076321 A1 | 3/2010 | Zhang et al. |
| 2011/0060714 A1* | 3/2011 | Ukawa ................... A61B 5/021 706/52 |
| 2011/0196217 A1 | 8/2011 | Myoujou et al. |
| 2012/0253207 A1 | 10/2012 | Sarkar et al. |
| 2012/0259183 A1 | 10/2012 | Thakur et al. |
| 2015/0138205 A1* | 5/2015 | Rajagopalan .......... A61B 5/742 345/440 |
| 2015/0327776 A1 | 11/2015 | Zhang et al. |
| 2015/0342540 A1 | 12/2015 | An et al. |

FOREIGN PATENT DOCUMENTS

| | | |
|---|---|---|
| CN | 107920743 A | 4/2018 |
| EP | 1102200 A2 | 5/2001 |
| EP | 2182846 A1 | 5/2010 |
| EP | 2333527 A1 | 6/2011 |
| EP | 2361035 A1 | 8/2011 |
| JP | 2010082009 A | 4/2010 |
| JP | 2010532208 A | 10/2010 |
| JP | 2011056018 A | 3/2011 |
| JP | 2011147493 A | 8/2011 |
| JP | 2012502752 | 2/2012 |
| JP | 2018524079 A | 8/2018 |
| WO | WO-2009005559 A1 | 1/2009 |
| WO | WO-2010033699 A1 | 3/2010 |
| WO | WO-2010035811 A1 | 4/2010 |
| WO | WO-20100113888 A1 | 5/2010 |
| WO | WO-2010111349 A1 | 9/2010 |
| WO | WO-2010132311 A1 | 11/2010 |
| WO | WO-2014035836 A1 | 3/2014 |
| WO | WO-2016210063 A1 | 12/2016 |

OTHER PUBLICATIONS

"International Application Serial No. PCT/US2016/038915, International Preliminary Report on Patentability dated Jan. 4, 2018", 31 pgs.

"International Application Serial No. PCT/US2016/038915, International Search Report dated Sep. 16, 2016", 5 pgs.

"International Application Serial No. PCT/US2016/038915, Written Opinion dated Sep. 16, 2016", 8 pgs.

"European Application Serial No. 16742075.1, Response filed Aug. 24, 2018 to Communication Pursuant to Rules 161 and 162 EPC dated Feb. 22, 2018", 20 pgs.

"Japanese Application Serial No. 2017-566760, Notification of Reasons for Refusal dated Dec. 18, 2018", W/ English Translation, 7pgs.

"Australian Application Serial No. 2016282695, Response filed Oct. 9, 2018 to First Examination Report dated May 2, 2018", 18 pgs.

"Japanese Application Serial No. 2017-566760, Response filed Mar. 15, 2019 to Notification of Reasons for Refusal dated Dec. 18, 2018", w/ English claims, 10 pgs.

\* cited by examiner

EVENT DETECTION USING A VARIABLE THRESHOLD

CLAIM OF PRIORITY

This application claims the benefit of priority under 35 U.S.C. § 119(e) of U.S. Provisional Patent Application Ser. No. 62/184,021, filed on Jun. 24, 2015, which is herein incorporated by reference in its entirety heart failure.

TECHNICAL FIELD

This document relates generally to medical devices, systems, and methods, and more particularly, to systems, devices and methods for detecting and monitoring for an event such as worsening heart failure.

BACKGROUND

Many diseases require complex health care regimens and affect large numbers of people. For example, congestive heart failure (CHF) is a major health problem and affects over five million people in the United States alone. CHF is the loss of pumping power of the heart, resulting in the inability to deliver enough blood to meet the demands of peripheral tissues. CHF patients typically have enlarged heart with weakened cardiac muscles, resulting in reduced contractility and poor cardiac output of blood.

CHF is usually a chronic condition, but can occur suddenly. It can affect the left heart, right heart or both sides of the heart. If CHF affects the left ventricle, signals that control the left ventricular contraction can be delayed, which can result in the left and right ventricles not contracting simultaneously. Non-simultaneous contractions of the left and right ventricles further decrease the pumping efficiency of the heart.

OVERVIEW

Detection of clinically meaningful events using sensed data can reduce health care costs and improve patient well-being when appropriate therapy regimen modifications are made in a timely manner. Clearly communicating the status of a patient and the onset of an event can be helpful for both the patient and the healthcare system.

For example, frequent monitoring of CHF patients and timely detection of events indicative of worsening heart failure (HF) can help prevent HF decompensation events in CHF patients, which can reduce costs associated with HF hospitalization. In addition, the identification of patients at an elevated risk of developing future HF events can help ensure timely treatment, thereby improving the prognosis and patient outcome. For example, identifying and safely managing the patients having risk of future HF events can avoid unnecessary medical intervention and reduce healthcare costs.

Ambulatory medical devices can be used for monitoring HF patients and detecting worsening HF, which can lead to decompensation events if left untreated. Examples of such ambulatory medical devices can include implantable medical devices (IMD), subcutaneous medical devices, wearable medical devices and other external medical devices. The ambulatory or implantable medical devices can include physiologic sensors which can be configured to sense electrical activity, mechanical function of the heart, or physical or physiological variables associated with the signs and symptoms of worsening HF. An ambulatory medical device used for monitoring HF patients can also optionally deliver therapy, such as electrical stimulation pulses to a target area, which can, for example, restore or improve the cardiac function or neural function. Some of these devices can also include diagnostic features, which can, for example, use transthoracic impedance, or other sensor signals. For example, fluid accumulation in the lungs decreases the transthoracic impedance due to the lower resistivity of the fluid than air in the lungs. Fluid accumulation in the lungs can also irritate the pulmonary system and leads to decrease in tidal volume and increase in respiratory rate. Fluid accumulation in the lungs can be detected by measuring transthoracic impedance.

An example method of monitoring the status of a heart failure patient to drive a therapy regimen includes collecting at least two samples of at least one physiologic parameter associated with heart failure, determining a first patient trend using the at least two samples, indicating that an onset threshold level is active, and comparing the first patient trend to the onset threshold level. When the first patent trend exceeds the onset threshold level, the method continues to collect samples after the trend exceeds the onset threshold level and determines a second patient trend using the samples detected after the first trend exceeds the onset threshold. In some examples, the method can include indicating that a reset threshold level is active, the reset threshold level being different than the onset threshold level. The second patient trend can be compared to the reset threshold. When the second patient trend falls below the reset threshold, the reset threshold can be deactivated. The onset threshold can optionally be reactivated when the reset threshold is deactivated. In some examples, a different threshold is activated. In an example, when the second patient trend falls below the reset threshold, an output such as a display can be modified to indicate to a user that the reset threshold level is no longer active. In an example, the method includes displaying a visual representation of the first patient trend, second patient trend, onset threshold level, and reset threshold level. A difference between the onset threshold level and reset threshold level can form a visually detectable change, such as a step, that can be indicative of a patient alert that occurs when first patient trend exceeds the onset threshold level. In some examples, the method includes delivering an alert that a patient therapy regimen should be adjusted and adjusting the patient therapy regimen in response to the alert.

In addition or alternatively, an example method can include monitoring the status of a patient by receiving at least two samples of at least one physiologic parameter associated with heart failure, determining a first trend using the at least two samples, and comparing the trend to a first threshold. The method can further include declaring a beginning of a patient alert period when the trend exceeds the first threshold, continuing to receive samples after the trend exceeds the first threshold, determining a second trend using the samples detected after the trend exceeds the threshold, and comparing the second trend to a second threshold that is lower than the first threshold. An end to the patient alert period can be declared when the second trend falls below the second threshold.

In some examples, specified information, such as the beginning and end of the patient alert period, can be stored in the device and available for review by an external device such as a programmer. For example, the beginning and end of the patient alert period can be stored in an implantable diagnostic or therapy device, and later output to a communicator or programmer that is designed to work with the device.

In some examples, the degree to which one or more physiologic parameters are responsible for change in a composite index can be presented on a display or otherwise communicated to a user.

An example patient monitoring system can include an implantable or wearable device that includes a sense circuit configured to receive at least two samples, a memory configured to store the at least two samples, and a physiologic data analyzer circuit configured to determine a first trend using the at least two samples and compare the trend to a first threshold. The implantable or wearable device can declare a beginning of a patient alert period when the trend exceeds the first threshold. The device can continue to receive samples through the sense circuit after the trend exceeds the first threshold. In an example, the physiologic data analyzer circuit can be configured to determine a second trend using the samples detected after the trend exceeds the first threshold, compare the second trend to a second threshold that is lower than the first threshold, and, when the second trend falls below the second threshold, declare an end to the patient alert period. In some examples, the system can be configured to determine a dynamic threshold that varies based on time or a sensed physiologic parameter. In some examples, the beginning and end of the patient alert period can be stored in the device and available for review by an external device such as a programmer.

A non-limiting number list of examples follows.

Example 1 can include or use subject matter (e.g. process, apparatus, article of manufacture, system, etc.) that can include or use a method of monitoring the status of a heart failure patient. The method comprising can include collecting at least two samples of at least one physiologic parameter associated with heart failure, determining a first patient trend using the at least two samples, and indicating that an onset threshold level is active. Example 1 can further include comparing the first patient trend to the onset threshold level and, when the first patent trend exceeds the onset threshold level, continuing to collect samples after the trend exceeds the onset threshold level, determining a second patient trend using the samples detected after the first trend exceeds the onset threshold, and indicating that a reset threshold level is active, the reset threshold level different than the onset threshold level. Example 1 can further include comparing the second patient trend to the reset threshold, and, when the second patient trend falls below the reset threshold, indicating that the reset threshold level is no longer active.

Example 2 can include or use or can be combined with the subject matter of Example 1 to include or use presenting a visual representation of the first patient trend and second patient trend over time, where indicating that an onset threshold level is active can include showing the onset level on the visual representation time-aligned with the first patient trend.

Example 3 can include or use or can be combined with the subject matter of any one or any combination of Examples 1-2 to include or use presenting on the visual representation the reset threshold level and aligning the reset threshold level with the second patient trend on a time axis.

Example 4 can include or use or can be combined with the subject matter of any one or any combination of Examples 1-3 to include or use, the indicating that a reset threshold level is active includes shading or highlighting an area between the second trend and the reset threshold, an area between the onset threshold and the first trend, or an area above the reset threshold and above the onset threshold.

Example 5 can include or use or can be combined with the subject matter of any one or any combination of Examples 1-4 to include or use displaying a visual representation of the first patient trend, second patient trend, onset threshold level, and reset threshold level, wherein a difference between the onset threshold level and reset threshold level forms a visually detectable change indicative of a patient alert period that starts when first patient trend exceeds the onset threshold level and ends when second patient trend falls below the reset threshold level.

Example 6 can include or use or can be combined with the subject matter of any one or any combination of Examples 1-5 to include or use declaring an alert that a patient therapy regimen should be adjusted.

Example 7 can include or use or can be combined with the subject matter of any one or any combination of Examples 1-6 to include or use receiving an onset input to adjust the onset threshold level and receiving a reset input to adjust the reset threshold level, where the monitoring of the patient is adjustably configurable using the onset input and the reset input.

Example 8 can include or use or can be combined with the subject matter of any one or any combination of Examples 1-7 to include or use receiving a threshold input to simultaneously adjust the onset threshold level and the reset threshold value, and receiving an offset input to adjust an offset between the onset threshold level and the reset threshold level, wherein the monitoring of the patient is adjustably configurable using the threshold input and the offset input.

Example 9 can include or use or can be combined with the subject matter of any one or any combination of Examples 1-8 to include or use, when the first patient trend exceeds the onset threshold level, declaring a beginning of a patient alert period, and when the second patient trend falls below the reset threshold, declaring an end to the patient alert period.

Example 10 can include or use or can be combined with the subject matter of any one or any combination of Examples 1-9 to include or use the reset threshold varies as a function of which physiologic parameter dominates a change in the composite index.

Example 11 can include or use or can be combined with the subject matter of any one or any combination of Examples 1-10 to include or use indicating the degree to which one or more physiologic parameters are responsible for a change in the composite index.

Example 12 can include or use or can be combined with the subject matter of any one or any combination of Examples 1-11 the reset threshold varies as a function of time.

Example 13 can include or use or can be combined with the subject matter of any one or any combination of Examples 1-12 to include or use a patient monitoring system that can include a sense circuit configured to receive at least two samples, a memory configured to store the at least two samples, and a physiologic data analyzer circuit configured to determine a first trend using the at least two samples and compare the trend to a first threshold. The physiologic data analyzer circuit can configured to, when the trend exceeds the first threshold, declare a beginning of a patient alert period, and continue to receive samples through the sense circuit after the trend exceeds the first threshold. The physiologic data analyzer circuit can be further configured to determine a second trend using the samples detected after the trend exceeds the threshold, compare the second trend to a second threshold that is lower than the first threshold, and, when the second trend falls below the second threshold, declare an end to the patient alert period.

Example 14 can include or use or can be combined with the subject matter of any one or any combination of Examples 1-13 to include or use an implantable or wearable device, the implantable or wearable device including the physiologic data analyzer circuit. The beginning and end of the patient alert period can be stored in the implantable or wearable device and can be available for review using an external device such as a programmer. The implantable or wearable device can, for example, be a pacemaker, a defibrillator, a cardiac resynchronization (CRT) device, or a diagnostic device.

Example 15 can include or use or can be combined with the subject matter of any one or any combination of Examples 1-14, to include or use the physiologic data analyzer circuit is further configured to determine a dynamic threshold that varies based on time or a sensed physiologic parameter.

Example 16 can include or use or can be combined with the subject matter of any one or any combination of Examples 1-15 to include or use a method of monitoring the status of a heart failure patient to drive a therapy regimen. The method can include collecting at least two samples of at least one physiologic parameter associated with heart failure, determining a first patient trend using the at least two samples, indicating that an onset threshold level is active, comparing the first patient trend to the onset threshold level, when the first patent trend exceeds the onset threshold level, continuing to collect samples after the trend exceeds the onset threshold level, determining a second patient trend using the samples detected after the first trend exceeds the onset threshold, indicating that a reset threshold level is active, the reset threshold level different than the onset threshold level, comparing the second patient trend to the reset threshold, and, when the second patient trend falls below the reset threshold, indicating that the reset threshold level is no longer active.

Example 17 can include or use or can be combined with the subject matter of any one or any combination of Examples 1-16 to include or use presenting a visual representation of the first patient trend and second patient trend over time, where indicating that an onset threshold level is active comprises showing the onset level on the visual representation time-aligned with the first patient trend.

Example 18 can include or use or can be combined with the subject matter of any one or any combination of Examples 1-17 to include or use indicating that an onset threshold level is active comprises representing the patient trend or the onset threshold level using one or more of a color, a line thickness, a line type or by not displaying the first patient trend when the onset level is active.

Example 19 can include or use or can be combined with the subject matter of any one or any combination of Examples 1-18 to include or use presenting on the visual representation the reset threshold level and aligning the reset threshold level with the second patient trend on a time axis.

Example 20 can include or use or can be combined with the subject matter of any one or any combination of Examples 1-19 to include or use indicating that a reset threshold level is active comprises shading or highlighting an area between the second trend and the reset threshold, an area between the onset threshold and the first trend, or an area above the reset threshold and above the onset threshold.

Example 21 can include or use or can be combined with the subject matter of any one or any combination of Examples 1-20 to include or use displaying a visual representation of the first patient trend, second patient trend, onset threshold level, and reset threshold level, where a difference between the onset threshold level and reset threshold level forms a visually detectable change indicative of a patient alert period that starts when first patient trend exceeds the onset threshold level and ends when second patient trend falls below the reset threshold level.

Example 22 can include or use or can be combined with the subject matter of any one or any combination of Examples 1-21 to include or use declaring an alert that a patient therapy regimen should be adjusted and adjusting the patient therapy regimen in response to the alert.

Example 23 can include or use or can be combined with the subject matter of any one or any combination of Examples 1-22 to include or use receiving an onset input to adjust the onset threshold level and receiving a reset input to adjust the reset threshold level, wherein the monitoring of the patient is adjustably configurable using the onset input and the reset input.

Example 24 can include or use or can be combined with the subject matter of any one or any combination of Examples 1-23 to include or use receiving a threshold input to simultaneously adjust the onset threshold level and the reset threshold value, and receiving an offset input to adjust an offset between the onset threshold level and the reset threshold level, where the monitoring of the patient is adjustably configurable using the threshold input and the offset input.

Example 25 can include or use or can be combined with the subject matter of any one or any combination of Examples 1-24 to include or use a method of monitoring the status of a patient. The method can include receiving at least two samples of at least one physiologic parameter associated with heart failure, determining a first trend using the at least two samples, comparing the trend to a first threshold, and, when the trend exceeds the first threshold, declaring a beginning of a patient alert period. The method can further include continuing to receive samples after the trend exceeds the first threshold, determining a second trend using the samples detected after the trend exceeds the threshold, comparing the second trend to a second threshold that is lower than the first threshold, and, when the second trend falls below the second threshold, declaring an end to the patient alert period.

Example 26 can include or use or can be combined with the subject matter of any one or any combination of Examples 1-25 to include or use receiving at least two samples comprises detecting at least two samples of two or more physiologic parameters, and wherein determining a first trend comprises determining a trend of a composite index of the two or more physiologic parameters.

Example 27 can include or use or can be combined with the subject matter of any one or any combination of Examples 1-26, to include or use the second threshold varies as a function of which physiologic parameter dominates a change in the composite index.

Example 28 can include or use or can be combined with the subject matter of any one or any combination of Examples 1-27 to include or use indicating the degree to which one or more physiologic parameters are responsible for a change in the composite index.

Example 29 can include or use or can be combined with the subject matter of any one or any combination of Examples 1-28, to include or use the second threshold varies as a function of time.

Example 30 can include or use or can be combined with the subject matter of any one or any combination of Examples 1-29 to include or use a patient monitoring system that can include a sense circuit configured to receive at least two samples, a memory configured to store the at least two samples, and a physiologic data analyzer circuit configured to determine a first trend using the at least two samples and compare the trend to a first threshold. The physiologic data analyzer circuit can configured to, when the trend exceeds the first threshold, declare a beginning of a patient alert period, and continue to receive samples through the sense circuit after the trend exceeds the first threshold. The physiologic data analyzer circuit can be further configured to determine a second trend using the samples detected after the trend exceeds the threshold, compare the second trend to a second threshold that is lower than the first threshold, and, when the second trend falls below the second threshold, declare an end to the patient alert period.

Example 31 can include or use or can be combined with the subject matter of any one or any combination of Examples 1-30 to include or use an implantable or wearable device, the implantable or wearable device including the physiologic data analyzer circuit.

Example 31 can include or use or can be combined with the subject matter of any one or any combination of Examples 1-30 to include or use the beginning and end of the patient alert period can be stored in the implantable or wearable device and are available for review using an external device such as a programmer. The implantable or wearable device can be a pacemaker, a defibrillator, a cardiac resynchronization (CRT) device, or a diagnostic device.

Example 33 can include or use or can be combined with the subject matter of any one or any combination of Examples 1-32 to include or use the physiologic data analyzer circuit is further configured to determine a dynamic threshold that varies based on time or a sensed physiologic parameter.

Example 34 can include or use or can be combined with the subject matter of any one or any combination of Examples 1-33 to include or use an external device communicatively coupled to the implantable or wearable device, wherein the implantable or wearable medical is configured to communicate the beginning and end of the alert period to the external device.

Example 35 can include or use or can be combined with the subject matter of any one or any combination of Examples 1-34 to include or use the external device include a graphical display configured to show the first threshold and periods where the first threshold is exceeded.

This section is intended as an overview of some of the teachings of the present application and not intended to be an exclusive or exhaustive treatment of the present subject matter. Further details about the present subject matter are found in the detailed description and appended claims. Other aspects of the present disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for notifying a health care professional regarding a meaningful change in the physiologic state of a patient, such as changes that indicate that a patient is or may be experiencing worsening of HF. Early detection and notification of such an event can allow modification of a therapy regiment to avoid a subsequent event, such as HF decompensation. Use of a variable threshold to trigger the beginning of a patient alert period and a subsequent end of the patient event period, which can promote more useful definition of patient event periods around physiologic events, such as worsening heart failure. In some examples, use of a variable threshold can provide a visual indication of the beginning or end of a patient alert period. For example, a step down in the variable threshold can be identified by the unaided human eye on a plot of an index against time. Use of a variable threshold can also avoid a series of short alert periods when a physiologic value or index value remains close to an onset threshold value, which can result in a series that threshold crossings that can activate and deactivate an alert period status.

Figure 1:
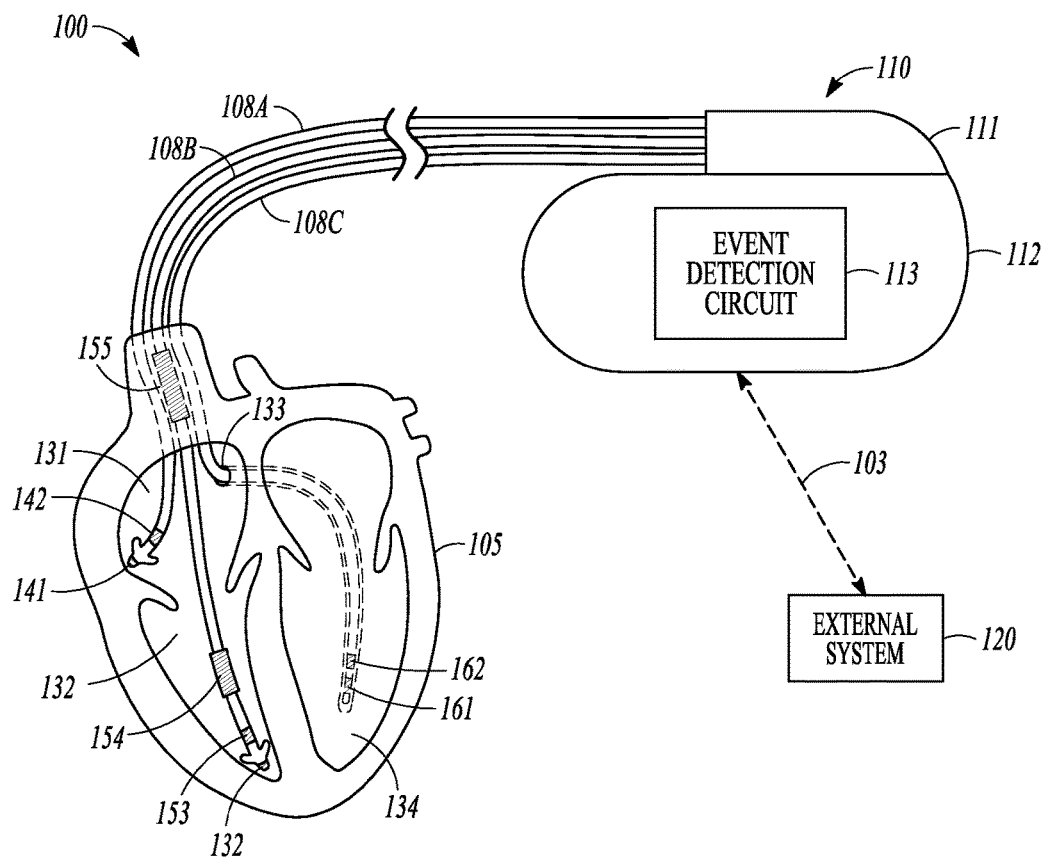
FIG. 1 illustrates an example of a cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) that can be electrically coupled to a heart 105 such as through one or more leads 108A-C, and an external system 120 that can communicate with the IMD 110 such as via a communication link 103. The IMD 110 can include an implantable cardiac device such as a pacemaker, an implantable cardioverter-defibrillator (ICD), or a cardiac resynchronization therapy defibrillator (CRT-D), for example. The IMD 110 can alternatively be or include one or more monitoring or therapeutic devices such as a subcutaneously implanted device, a wearable external device, a neural stimulator, a drug delivery device, a biological therapy device, a diagnostic device, or one or more other ambulatory medical devices. In some examples, all or portions of the IMD 110 may be coupled to, or may be substituted by, a monitoring medical device such as a wearable, bedside or other external monitor.

As illustrated in FIG. 1, the IMD 110 can include a hermetically sealed housing 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two or more leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of surface or subcutaneous electrocardiogram, intracardiac electrogram, ECG, cardiac contractility, arrhythmia information, pacing prevalence, heart rate, heart rate variability, intrathoracic impedance, intracardiac impedance, local impedance, respiration information, e.g. one or more respiration signals such as a respiration rate signal, a tidal volume signal, a minute ventilation signal, or rapid shallow breathing index (RR/TV) signal, apnea-hypopnea index, arterial pressure, pulmonary artery pressure, left atrial pressure, LV pressure, RV pressure, LV coronary pressure, coronary blood temperature, blood oxygen saturation, one or more heart sounds, physical activity or exertion level, physiologic response to activity, patient's posture, physiological response to patient posture, patient's body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include an event detection circuit 113. In an example, the event detection circuit 113 can receive one or more patient information sources such as one or more physiologic signals and process the information to ascertain whether an event, such as worsening heart failure, may have occurred or be occurring. In an example, the event detection circuit 113 can be coupled to one or more ambulatory physiologic sensors deployed on or within the patient and communicated with the IMD 110, such as electrodes on one or more of the leads 108A-C and the can 112, or ambulatory physiologic sensors deployed on or within the patient and communicated with the IMD 110.

In an example, the event detection circuit 113 can combine two or more sources of patient information (e.g. transthoracic impedance, respiration, activity, heart sounds or any of the other physiologic parameters identified herein) into a composite index and compares a composite index value to a threshold. In various examples, the event detection computes or receives one or more of a transthoracic impedance index, a fluid index, and apnea hypopnea index, or a decompensation index and compares the index to a threshold.

When the threshold is exceeded, the event detection circuit generates an alert or otherwise indicates that the threshold has been exceeded. In some examples, the event detection circuit 113 compares a single source of patient information (e.g. transthoracic impedance, respiration, activity, or heart sounds) to a threshold, or generates an index from a single source of information and compares the index to a threshold. After the threshold has been exceeded, the event detection circuit 113 activates a new threshold that is different than the previously-used threshold. In an example, the new threshold is lower than the previous threshold. In various examples, when the monitored value— e.g. the patient information, index, or composite index— falls below the new threshold, a patient alert period is terminated, an alert is cancelled, an indication that the previous threshold has been exceeded is terminated, or an indication that the monitored value has fallen below the new threshold is delivered.

This two-threshold system can be helpful to a health care provider because it can tend reduce the occurrence of repeated short alert periods that can occur when a trend varies above and below a threshold value. It can also tends to avoid premature termination of an alert if a patient's status improves for a short time but does not fully recover to a previous normal or baseline.

In an example, the system 100 includes an external system 120. The external system 120 can, for example, allow for programming of the IMD 110 and can receive information about one or more signals acquired by IMD 110, such as can be received via a communication link 103. The external system 120 can, for example, include a local external IMD programmer. In some examples, the external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

In an example, the event detection circuit 113 can be implemented or duplicated at the external system 120, which can be configured to perform some or all of the event detection, such as using data extracted from the IMD 110 or data stored in a memory within the external system 120.

In some examples, the event detection circuit 113 can include multiple sub-circuits that perform functions such as sensing, determining therapy, or processing information. In some examples, portions of event detection circuit 113 may be distributed between the IMD 110 and the external system 120. In some examples, the event detection circuit 113 is not purely a hardware circuit: In an example, the event detection circuit 113 includes a microprocessor and a memory storing instructions to be carried out by the microprocessor to provide the event detection.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device, a banded device such as a watch, clothing), or other external medical device that removably attachable to a person.

Figure 2:
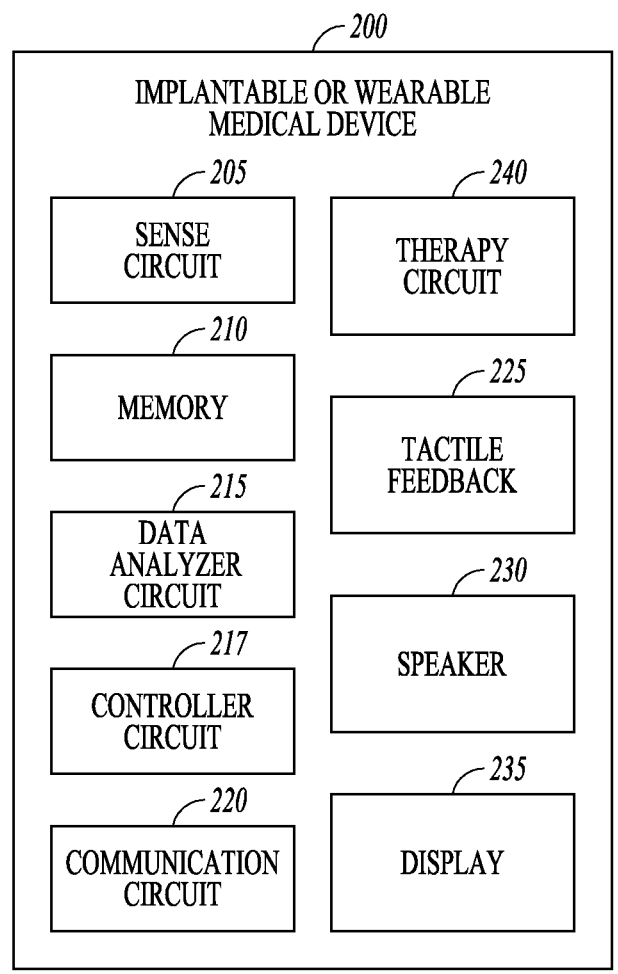
FIG. 2 illustrates an example of an implantable or wearable device.

FIG. 2 illustrates an example of an implantable or wearable device 200, such as an implantable loop recorder, a pacemaker or defibrillator, a neurostimulator, a watch, a garment, a patch-based sensing device or other device adhered or connected to the body and configured to receive physiologic information from a patient. In an example, the implantable or wearable device 200 is the IMD 110 described above and shown in FIG. 1.

Returning to FIG. 2, the example implantable or wearable device 200 can include one or more of a sense circuit 205, a memory 210, a physiologic data analyzer circuit 215, a controller circuit 217, a communication circuit 220, and a therapy circuit 240. The implantable or wearable device 200 can also include a tactile feedback element 225, a speaker 230, or a display 235.

The sense circuit 205 receives information about at least one physiologic parameter of a patient. The physiologic information is stored in memory 210. In an example, the memory stores the physiologic information, or one or more indices derived therefrom, and later provides the stored information upon request to the physiologic data analyzer circuit 215. In an example, the controller circuit 217 can control the operations of the various circuits and components as well as the data flow and instructions among the circuits and components. In an example, the sense circuit 205, memory 210, and physiologic data analyzer circuit 215 form the event detection circuit 113 described above.

The sense circuit 205 receives one or more physiologic signals obtained from a patient. The physiologic signals can be sensed using one or more ambulatory physiologic sensors, or using one or more external sensors or testing devices communicatively coupled to the patient information receiver circuit 205. Examples of such a physiologic signal can include one or more of surface or subcutaneous electrocardiograph (ECG), electrograms such as sensed using electrodes from one or more of the leads 108A-C or the can 112, ECG, cardiac contractility, pacing prevalence, heart rate, heart rate variability, arrhythmia information, intrathoracic impedance, intracardiac impedance, apnea-hypopnea index, arterial pressure, pulmonary artery pressure, left atrial pressure, LV pressure, RV pressure, LV coronary pressure, coronary blood temperature, body core temperature, blood oxygen saturation, one or more heart sounds, systolic time intervals, heart sound based cardiac time intervals, impedance based cardiac time intervals, physiologic response to activity, physical activity or exertion level, night-time restlessness, patient's posture, physiological response to patient posture, patient's weight, one or more respiration signals such as a respiration rate signal, a tidal volume signal, a minute ventilation signal, or rapid shallow breathing index (RR/TV) signal. The physiologic signals can also include one or more of brain natriuretic peptide (BNP), blood panel, sodium and potassium levels, glucose level and other biomarkers and bio-chemical markers. The physiologic signals can also include device therapy statistics such as a percentage of biventricular or left-ventricular only pacing in patient with ambulatory medical devices.

In an example, the physiologic data analyzer circuit 215 compares the physiologic information obtained by the sense circuit against a threshold, also stored in memory 210. In an example, the physiologic data analyzer circuit 215 computes an index using the physiologic information and compares the index against a threshold. In an example, the physiologic data analyzer circuit 215 combines multiples types of physiologic information (e.g. two or more of transthoracic impedance, respiration, activity, hearts sounds, and posture, or any other physiologic information identified herein) into a composite index and compares the composite index against a threshold. When a trend of physiologic information such as an index exceeds a threshold, the physiologic data analyzer circuit 215 may declare the beginning of an alert period. The physiologic data analyzer circuit 215 may then continue to compare trended information against another, different threshold—e.g. a higher or lower threshold—and declare an end to the alert period when the trend falls below the threshold. The physiologic data analyzer circuit 215 may also be configured to determine a dynamic trend based on one or more of time, physiologic information, or other information.

In an example, when the threshold is exceeded, the implantable or wearable device 200 communicates through the communication circuit 220 that the threshold has been exceeded to an external system, such that a health care professional can be alerted via a display, dashboard, email, text, fax, or other technical communication modality. Example displays for indicating that the threshold has been exceeded or that an alert period has been declared are shown in FIGS. 3A-3E. In an example, the implantable or wearable medical device 200 itself communicates that the threshold has been exceeded through the tactile feedback element 225, speaker 230, or display 235. In an example, the controller circuit 217 issues a command to the speaker or tactile feedback device to signal that the threshold has been exceeded, for example with a sound, verbal message, or vibration. In an example where a display is visible, such as on a wearable device such as a watch, phone, or patch, the controller circuit 217 issues a command to a display 235 to indicate that the threshold has been exceeded, such as the display of an alert.

In some examples the wearable or implantable medical device 200 can also retain and use previously-collected diagnostic information collected by the device, or by one or more additional ambulatory devices and communicated to the device through the communication circuit 220. In some examples, the device 200 may receive information collected or an index computed by one or more other devices through the communication circuit 220. In various examples, the device receives data physiologic data or computed indices such as fluid index or apnea hypopnea index.

The physiologic data analyzer circuit 215 can include one or more sub-circuits that can perform signal conditioning or pre-processing, including signal amplification, digitization, or filtering, on the one or more physiologic signals. The physiologic data analyzer circuit 215 can include a physiologic feature generator circuit configured to detect, from each of the one or more pre-processed physiologic signals, a respective physiologic feature indicative of patient physical or physiologic status. Examples of physiologic features can include mean, median, or other central tendency measures; a histogram of the signal intensity; a plurality of signal trends over time; one or more signal morphological descriptors; one or more signal change or rate of change features; one or more signal change or rate of change features, or signal power spectral density at a specified frequency range. The physiologic features can include components corresponding to physiologic activities. For example, the electrocardiogram or electrogram features can include P wave, R wave, T wave, QRS complex, or other components representing depolarization, hyperpolarization, repolarization, or other electrophysiological properties of the myocardium. The heart sound features can include relative timing (such as with respect to R wave), amplitude, or morphologic characteristics of one or more of S1, S2, S3, or S4 heart sounds. The impedance features can include maximum, minimum, mean, variance, rate of change, or other statistical or morphological features. The respiration signal features can include respiration rate, respiration depth, tidal volume, minute ventilation, rapid shallow breathing index (RR/TV), or other descriptors.

In some examples, implantable or wearable device 200 can receive a plurality of measurements of thoracic impedance value computed using a thoracic impedance signal such as sensed by the patient information receiver circuit 205. The cyclic variation of the thoracic impedance can be indicative of patient respiration. A statistical metric, such as a central tendency measure of the plurality of impedance measurements, can be computed to provide a statistical measure of patient prespiration strength, respiration rate, or respiration pattern. In some examples, the device 200 can receive a plurality of measurements of S3 heart sound intensity determined by using heart sound signals such as sensed by the patient information receiver circuit 205. A morphologic metric such as a change in S3 heart sound intensity from a baseline value can be computed. Such S3 intensity metric can be indicative of cardiac diastolic function change which is predictive of worsening HF. In various examples, sustained elevated values for a signal metric, or variability of the signal metric, may also be predictive of worsening HF.

Some examples and methods utilize signal metrics including a change in intrathoracic total impedance value (ITTI) from a reference value ($\Delta ITTI = ITTI - ITTI_{Ref}$), a change in respiration rate (RR) from a reference respiration rate ($\Delta RR = RR - RR_{Ref}$), a rate of change of RR ($\Delta RR/\Delta t$), and a change in a heart sound (HS) component such as S3 heart sound intensity from a reference level ($\Delta \|S3\| = \|S3\| - \|S3\|_{Ref}$). The ITTI can include a direct-current (DC) component of a wide-band intrathoracic impedance signal such as measured using two or more electrodes from one or more of the leads 108A-C or the can 112. In an example, voltage across electrode 153 and can 112 can be measured in response to electric current injected across electrode 154 and can 112, and the ITTI can be computed using Ohm's law. The reference levels, including $ITTI_{Ref}$, $RR_{Ref}$, and $\|S3\|_{Ref}$ can be determined using measurements of respective sensor signals during baseline when the patient is deemed free of the candidate conditions. Alternatively, the reference levels can be dynamically determined as a moving-average of respective signal metrics over a moving time window.

In various examples of creating a composite index, the index is formed using a model. The model comprises rules of assigning a higher diagnostic score to the candidate condition of "worsening HF" if (1) ITTI substantially decreases from the reference level by at least a threshold value, which indicates substantial intrathoracic fluid accumulation; (2) RR substantially increases from $RR_{Ref}$ by at least a threshold value, and $\Delta RR/\Delta t$ is within a threshold range, which indicates a gradual onset of increase in respiration rate; and (3)$\|S3\|$ substantially increases from the reference level by at least a threshold value. The model comprises rules of assigning a higher diagnostic score to the candidate condition of "pulmonary disease" if (1) RR substantially increases from the $RR_{Ref}$ by at least a threshold value and ΔRR/Δt exceeds a threshold range, which indicates a sudden onset in rise of respiration rate; or (2) $\|S3\|$ is within a threshold range around $\|S3\|_{Ref}$. As an example, the threshold for ΔRR can be approximately an increase of 2-4 breaths per minute, the threshold for ΔITTI can be approximately a decrease of 8-10% from a reference level, and the threshold for $\Delta\|S3\|$ can be approximately an increase of 0.3-0.5 milli-g.

In an example, the device 200 can adjust a therapy regimen in response to determining that a threshold has been crossed. Adjusting the therapy regimen can include, for example, one or more of adjusting cardiac stimulation parameters, adjusting neurostimulation parameters, and adjusting a pharmacological therapy regimen. In an example, adjusting the therapy regimen include automatically reconfiguring a cardiac resynchronization (CRT) therapy. In some examples, adjusting the therapy regimen includes initiation delivery of CRT therapy.

Figure 3A:
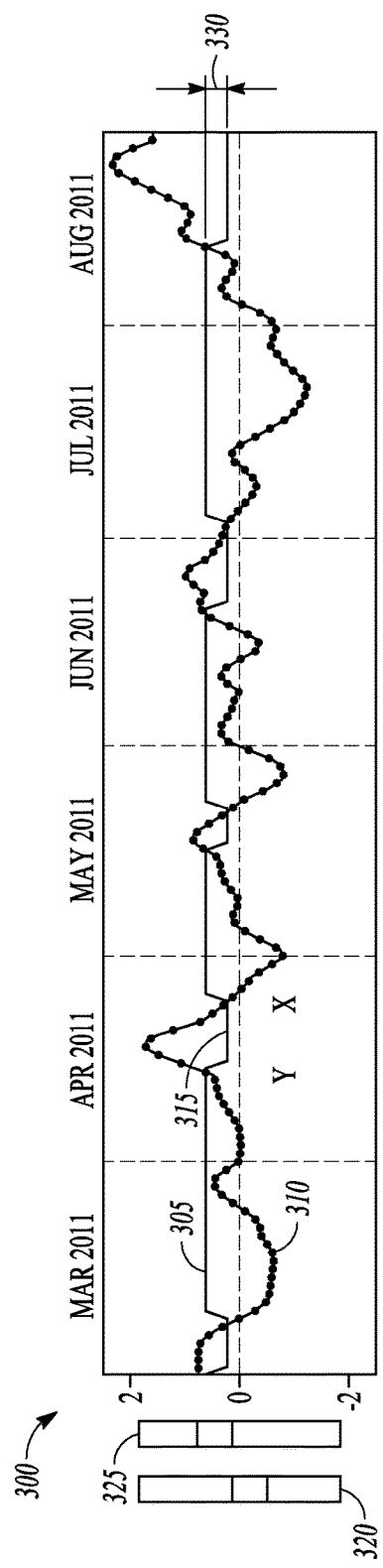
FIGS. 3A, 3B, 3C, 3D, and 3E illustrate example displays indicating trends passing above and below first and second thresholds.

Turning now to FIG. 3A, an example device provides a visual indication 300 of the threshold 305 that is active at a point in time. FIG. 3A shows an example trend 310 of a physiologic index for a patient over several months (March-August). At point X in mid-April, the trend 310 moves up past the threshold 305, suggesting that the onset of physiologic problem with the patient. In some examples, an alert is issued at this point, or the point is identified as the beginning of an alert period. A new lower threshold 315 is implemented at point X. The line 313 connecting the thresholds 305, 315 is provided for visual clarity and may optionally be presented or omitted. At point Y, the trend moves downward below threshold 315. In an example, the alert is cancelled at this point, or the point Y is identified as the end of the alert period X-Y. At point Y, the threshold is reset to the previous level (as shown), or set to a new level. At point Z, the trend 310 moves up past threshold 305 again, triggering another alert or alert period. In an example, the use of a technology-driven alert period permits communication of the alert period to other nodes in a healthcare system (e.g. doctors, nurses, EMR systems, or other devices) so that technical or human assessment of a patient can take into account the patient's status during the alert period.

In an example, the threshold levels are adjustable using graphical user interface (GUI) controls. In an example, slider element 320 controls the onset threshold 305, and slider element 325 controls reset threshold 315. In some examples, element 320 controls both threshold levels together, and element 325 controls the offset 330 between the levels. In an example, the elements 320 and 325 are "turnable" GUI knobs instead of sliders. In some examples in which the visual indication is provided on a touchscreen display, the thresholds themselves are selectable and slidable.

Figure 3B:
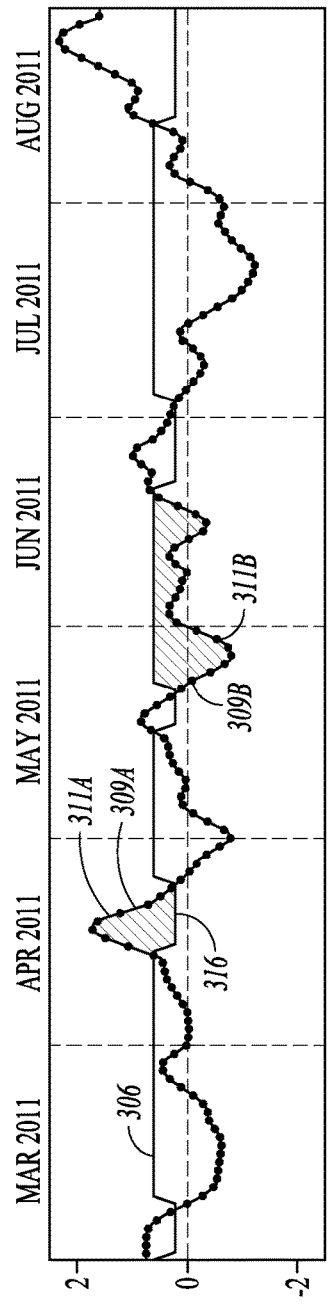

Turning to FIG. 3B, in an example, the visual indication 301 of onset thresholds 306 and reset threshold 316 may include shading 309A of the area under a curve defined by the trend 311A and the reset threshold 316. In some examples, the visual indication 301 of onset thresholds 306 and reset threshold 316 alternatively or additionally includes shading 309B of the area under a curve defined by the second trend 311B and the reset threshold 316. In some examples, two or more trends, e.g. trends for multiple sensors, are presented on the visual indication 301, with onset and reset thresholds shown for each trend.

Figure 3C:
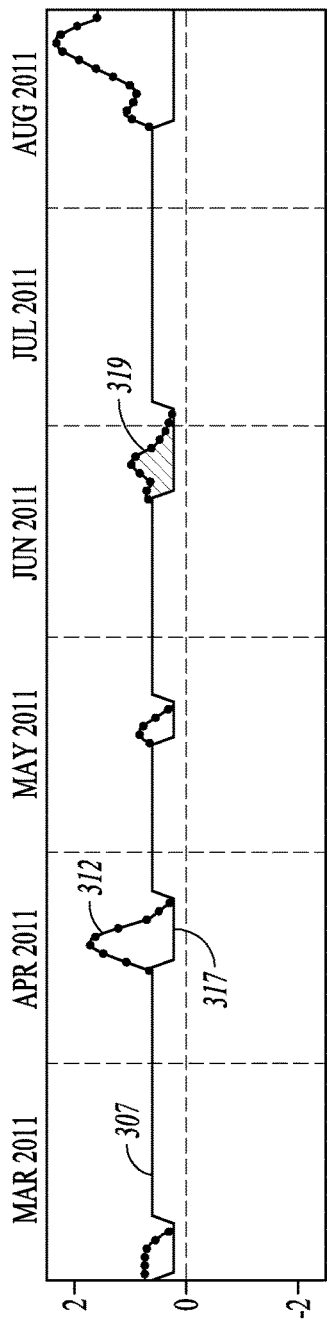

FIG. 3C illustrates an example where the trend 312 is visible only when it has exceeded onset threshold 307 and not receded below reset threshold 317.

Figure 3D:
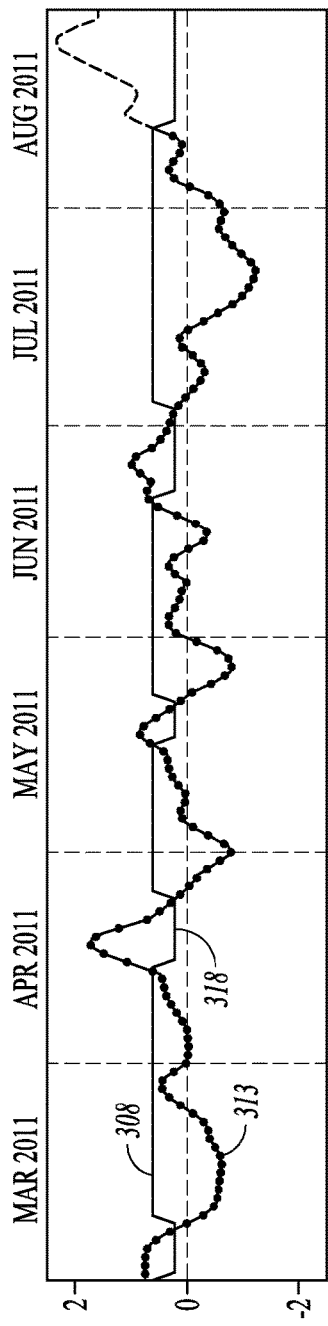

FIG. 3D illustrates an example where the portions of the trend 313 that have exceeded onset threshold 308 and not yet dropped below reset threshold 318 (i.e. alert periods are marked with a line type (e.g. dotted or dashed). In other examples alert periods are marked with a line weight or color.

Figure 3E:
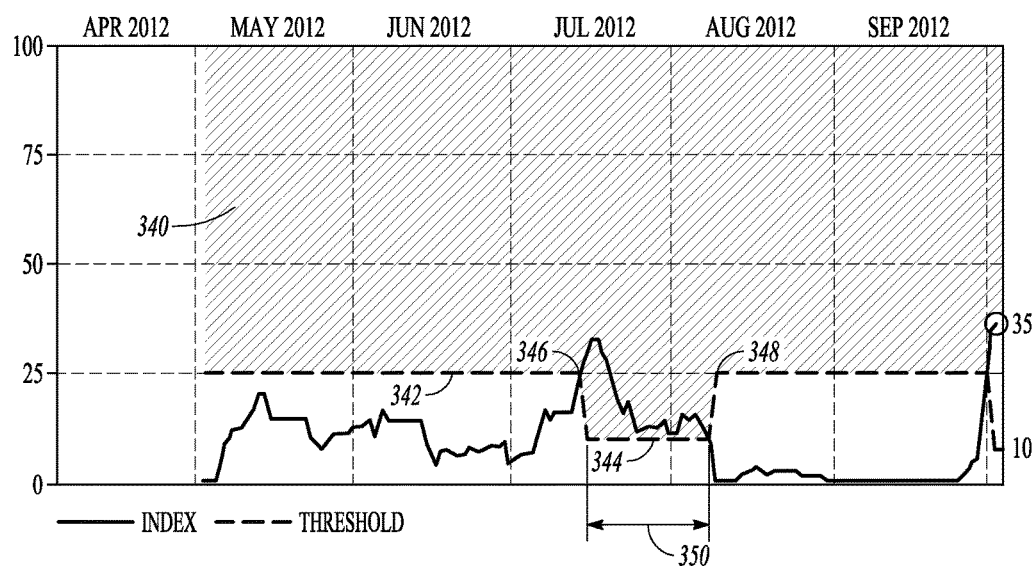

FIG. 3E illustrates an example display in which an area 340 above an onset threshold 342 and a reset threshold 344 is highlighted or shaded. The shading or highlighting of additional area on the display can indicate to a viewer that a reset threshold became active, at time 346, until time 348, at which point the onset threshold became active again. In some examples, the activation of the reset threshold can indicate that an alert period 350 was declared. An example method can include recommending adjustment of therapy when an alert period is declared, for example to treat a worsening heart failure patient. Some example methods can include adjusting a therapy when an alert period is declared, such as implementing a medical intervention for a heart failure patient to avoid a heart failure decompensation event. Some examples can include adjusting an operational parameter in a device, which can include adjusting a monitoring parameter, turning on a sensing feature, increasing a specificity or sensitivity parameter, or adjusting a therapy parameter in an implantable or wearable device.

Figure 4:
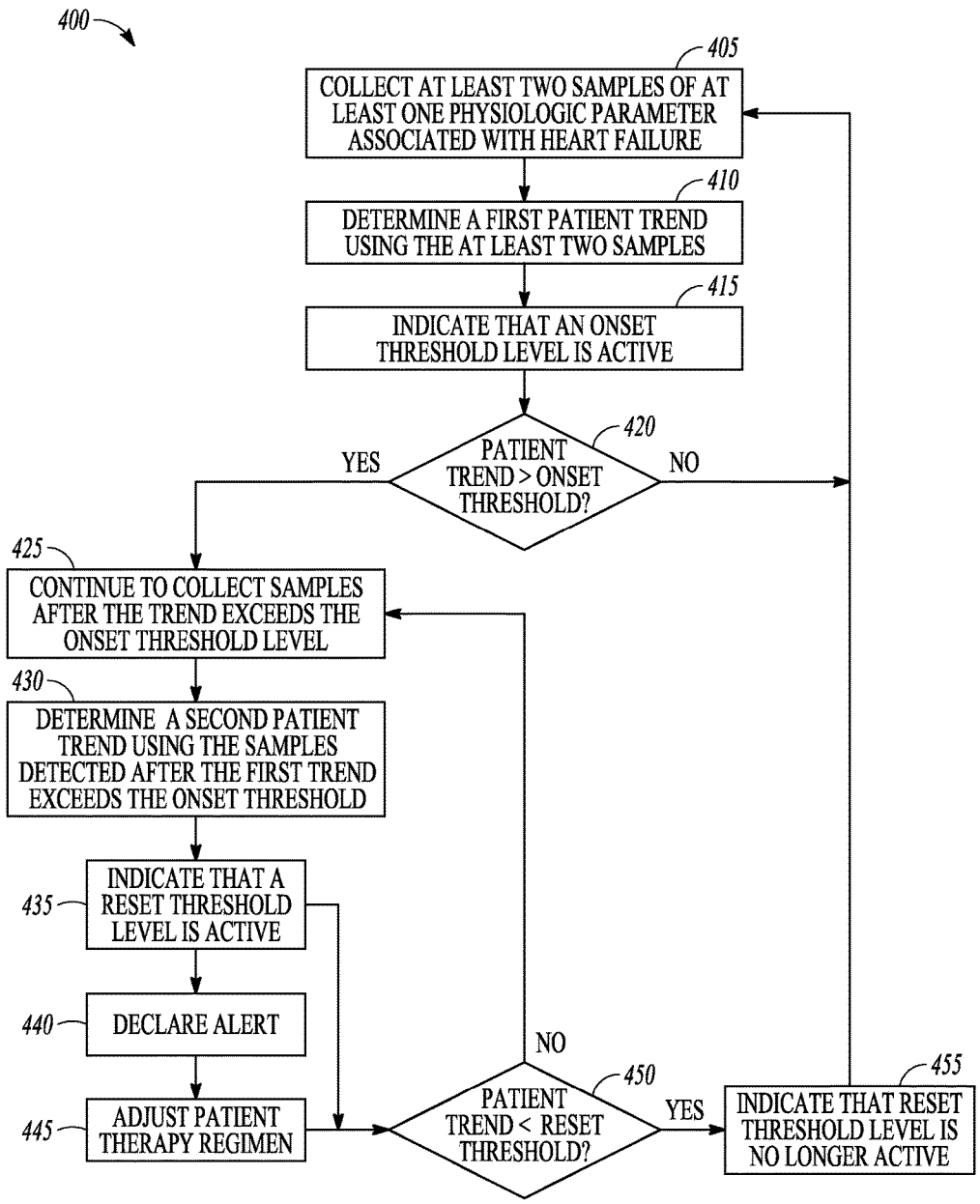
FIG. 4 illustrates an example method of monitoring the status of a heart failure patient to drive a therapy regimen.

FIG. 4 illustrates an example method 400 of monitoring the status of a heart failure patient to drive a therapy regimen. The method 400 can include at 405 collecting at least two samples of at least one physiologic parameter associated with heart failure. The collecting samples can include detecting a parameter using an implantable or wearable device, e.g. sensing a signal indicative of a physiologic parameter, or receiving samples previously collected, or collected. Examples of the physiological parameter can include a surface or subcutaneous electrocardiogram, intracardiac electrogram, arrhythmia information, heart rate, heart rate variability, local impedance, intrathoracic impedance, intracardiac impedance, respiration information, such as a respiration rate signal, a tidal volume signal, a minute ventilation signal, or rapid shallow breathing index (RR/TV) signal, arterial pressure, pulmonary artery pressure, left atrial pressure, RV pressure, LV coronary pressure, coronary blood temperature, blood oxygen saturation, one or more heart sounds, physical activity or exertion level, physiologic response to activity, patient's posture, patient's body weight, or body temperature.

The method 400 can include at 410 determining a first patient trend using the at least two samples. In an example, the patient trend can be displayed as shown in FIG. 3A, 3B, 3C, 3D, or 3E. In an example, determining a first patient trend includes determining a value at periodic intervals (e.g. once per second, once per minute, once per hour, once per day, or once per week, or once per month) and combining two of more values to create a trend, such as a line or curve.

The method 400 can include at 415 indicating that an onset threshold level is active. In an example, the onset level is displayed on a graph.

The method 400 can include at 420 comparing the first patient trend to the onset threshold level. When the first patent trend does not exceed the onset threshold level, the method returns to collecting samples at 405. When the first patent trend exceeds the onset threshold level, the method includes at 425 continuing to collect samples after the trend exceeds the onset threshold level, and at 430 determining a second patient trend using the samples detected after the first trend exceeds the onset threshold. The method can include at 435 indicating that a reset threshold level is active. The reset threshold level different than the onset threshold level. In an example, the reset threshold level is lower than the onset threshold level, which can prevent repeated alerts in a small period of time when the threshold hovers around the onset threshold level, or fluctuates due to compensatory mechanisms that may influence the trend level but not represent a full recovery. For example, during a heart failure episode such as decompensation, physiologic compensatory mechanisms may temporarily cause an improvement on a short period, but over a longer time course the patient's condition continues to deteriate. Using a lower reset threshold provides more assurance that the patient has actually recovered, and note merely temporarily improved due to the action of compensatory mechanisms.

The method can include at 440 optionally declaring an alert. In an example, the alert is communicated to a patient, a health care professional, or both. At 445, the method can include adjusting the therapy regimen in response to the trend exceeding the threshold. Variations can also be included. For example, the therapy regimen can be altered without declaring an alert (i.e. step 440 may be omitted.) Adjusting the therapy regimen can include, for example, one or more of adjusting cardiac stimulation parameters, adjusting neurostimulation parameters, and adjusting a pharmacological therapy regimen.

The method can include at 450 comparing the second patient trend to the reset threshold. When the second patient trend remains above the reset threshold, the method returns to collecting samples at 425. When the second patient trend falls below the reset threshold, the method can include at 455 indicating that the reset threshold level is no longer active. For example, an active threshold can be presented on a display, e.g. on onset threshold is shown correlated in time with deactivation of the reset threshold and activation of the onset threshold. In some examples, the trend of physiologic information such as a parameter or index is plotted when the trend is above the onset threshold, but is not shown when the trend is below the threshold.

In an example, the method includes presenting a visual representation of the first patient trend and second patient trend over time, and the onset level is shown on the visual representation time-aligned with the first patient trend. In an example, the reset threshold level is also shown on the visual representation.

In an example, the onset threshold level indicated to be active by representing the patient trend or the onset threshold level using one or more of a color, a line thickness, a line type or by not displaying the first patient trend when the onset level is active. In an example, a reset threshold level is indicated to be active by highlighting an area between the second trend and the reset threshold.

In an example, a difference between the onset threshold level and reset threshold level forms a visually detectable change, such as a step, that is indicative of a patient alert that occurs when first patient trend exceeds the onset threshold level.

In an example, the method includes receiving an onset input to adjust the onset threshold level and receiving a reset input to adjust the reset threshold level, wherein the monitoring of the patient is adjustably configurable using the onset input and the reset input. In some example, the method includes receiving a threshold input to simultaneously adjust the onset threshold level and the reset threshold value, and receiving an offset input to adjust an offset between the onset threshold level and the reset threshold level, wherein the monitoring of the patient is adjustably configurable using the threshold input and the offset input.

Figure 5:
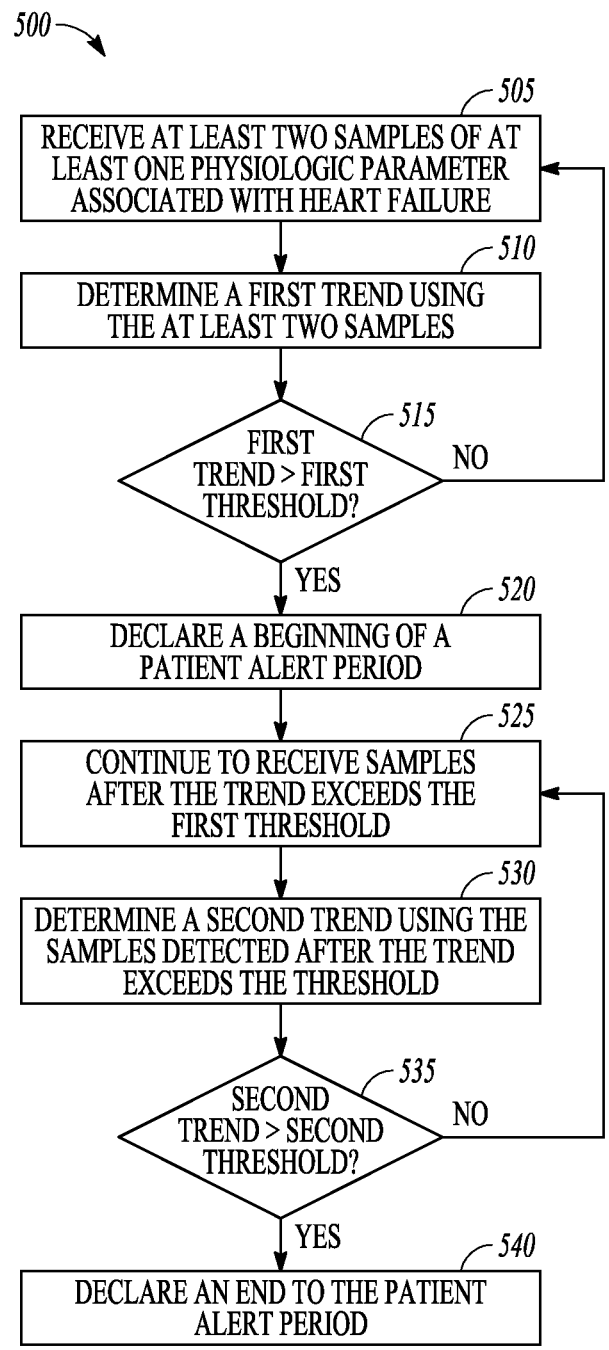
FIG. 5 illustrates an example method of monitoring the status of a patient and declaring the beginning and end of an alert period.

Turning now to FIG. 5, an example method 500 includes at 505 receiving at least two samples of at least one physiologic parameter associated with heart failure. In an example, receiving at least two samples includes detecting at least two samples of two or more physiologic parameters. The method can also include at 510 determining a first trend using the at least two samples and at 515 comparing the trend to a first threshold. In an example, determining a first trend includes determining a trend of a composite index of the two or more physiologic parameters.

At 515 the trend is compared to a threshold. When the trend is not greater than the threshold, the method returns to receiving samples at 505. When the trend exceeds the first threshold, the method includes at 520 declaring a beginning of a patient alert period, at 525 continuing to receive samples after the trend exceeds the first threshold, and at 530 determining a second trend using the samples detected after the trend exceeds the threshold.

The method can include at 530 comparing the second trend to a second threshold that is lower than the first threshold. In an example, the method includes determining a second threshold that varies as a function of which physiologic parameter dominates a change in the composite index. In an example the method include determining a second threshold that varies as a function of time. In an example, the second threshold increases as a function of time, which can correspond for example to establishment of a new baseline value of a physiologic parameter from a patient.

When the second trend remains above the second threshold, the method returns to receiving samples at 525. When the second trend falls below the second threshold, the method includes at 540 declaring an end to the patient alert period. In an example, the method also includes showing trend or threshold information on a display. In an example, trend or threshold information is shown correlated to time, e.g. over a course of days, weeks, or months. In an example, the method includes indicating on a display the degree to which one or more physiologic parameters are responsible for a change in the composite index.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the disclosure should be determined with reference to the appended claims, along with the full scope of equivalents to which such claims are entitled.

What is claimed is:

1. A method of operating a medical device system, the method comprising:
sensing physiological information of a subject using the medical device, the physiological information associated with heart failure of the subject;
determining a trend of the received physiological information; and
displaying one of an onset threshold indicative of onset of a physiological alert condition associated with heart failure or a reset threshold indicative of an end of the physiological alert condition according to a state of a medical device so that when the onset threshold is displayed the reset threshold is not displayed and vice versa, the method further comprising:
in a first state, comparing the determined trend to the onset threshold, and:
while the determined trend is below the onset threshold, displaying the onset threshold; and
when the determined trend exceeds the onset threshold, displaying the reset threshold and transitioning to a second state;
in the second state, comparing the determined trend to the reset threshold, and:
while the determined trend is above the reset threshold, displaying the determined trend and the reset threshold; and
when the determined trend falls below the reset threshold, displaying the onset threshold and transitioning to the first state.

2. The method of claim 1, wherein determining the trend of physiological information includes determining a first patient trend prior to a detection of the physiological alert condition using the onset threshold and a second patient trend after the detection using the onset threshold, and wherein the method further comprises presenting a visual representation of the first patient trend and second patient trend over time, and indicating that an onset threshold level is an active threshold by showing the onset level on the visual representation time-aligned with the first patient trend.

3. The method of claim 2, wherein indicating that an onset threshold level is the active threshold comprises representing the patient trend or the onset threshold level using one or more of a color, a line thickness, a line type, and not displaying the first patient trend when the onset threshold level is the active threshold.

4. The method of claim 2, further comprising presenting on the visual representation the reset threshold level as the active threshold and aligning the reset threshold level with the second patient trend on a time axis, and returning to indicating that the onset threshold value is the active threshold when the reset threshold is satisfied.

5. The method of claim 4, wherein indicating that a reset threshold level is the active threshold comprises shading or highlighting an area between the second trend and the reset threshold, an area between the onset threshold and the first trend, or an area above the reset threshold and above the onset threshold.

6. The method of claim 2, comprising displaying a visual representation of the first patient trend, second patient trend, onset threshold level, and reset threshold level, and displaying a difference between the onset threshold level and reset threshold level as a patient alert period that starts when the first patient trend exceeds the onset threshold level and ends when the second patient trend falls below the reset threshold level.

7. The method of claim 1, further comprising declaring an alert that a patient therapy regimen should be adjusted, and adjusting the patient therapy regimen in response to the alert.

8. The method of claim 1, further comprising receiving an onset input to adjust the onset threshold level and receiving a reset input to adjust the reset threshold level, wherein the monitoring of the patient is adjustably configurable using the onset input and the reset input.

9. The method of claim 1, further comprising receiving an threshold input to simultaneously adjust the onset threshold level and the reset threshold value, and receiving an offset input to adjust an offset between the onset threshold level and the reset threshold level, wherein the monitoring of the patient is adjustably configurable using the threshold input and the offset input.

10. A method of operating a medical device system, comprising:

sensing physiological information of a subject;
determining at least one physiologic parameter using the received physiological information;
determining a first trend of the at least one physiologic parameter using multiple samples of the received physiological information, the at least one physiologic parameter associated with heart failure;
displaying one of an onset threshold indicative of onset of a physiological alert condition associated with heart failure or a reset threshold indicative of an end of the physiological alert condition according to a state of the medical device so that when the onset threshold is displayed the reset threshold is not displayed and vice versa, the method further comprising:
in a first state, comparing the first trend to the onset threshold, and:
while the determined trend is below the onset threshold, displaying the onset threshold;
when the first trend exceeds the onset threshold, displaying the reset threshold and transitioning to a second state;
in the second state, determining a second trend of the at least one physiologic parameter using the samples detected after the first trend exceeds the onset threshold, comparing the second trend to a reset threshold that is lower than the onset threshold, and:
while the second determined trend is above the reset threshold, displaying the second determined trend and the reset threshold; and
when the determined second trend falls below the reset threshold, displaying the onset threshold and transitioning to the first state.

11. The method of claim 10, including determining two or more physiologic parameters using the multiple samples, and wherein determining a first trend comprises determining a trend of a composite index of the two or more physiologic parameters.

12. The method of claim 11, including varying the reset threshold as a function of which of the two or more physiologic parameters dominates a change in the composite index.

13. The method of claim 11, further comprising indicating the degree to which the two more physiologic parameters are responsible for a change in the composite index.

14. The method of claim 10, including varying the reset threshold as a function of time.

15. A patient monitoring system comprising:
a display;
a sense circuit configured to sense physiologic information of a subject, the physiological information associated with heart failure of the subject; and
a physiologic data analyzer circuit configured to:
receive the sensed physiological information of a subject, the physiological;
determine a trend of the received physiological information; and
display one of an onset threshold indicative of onset of a physiological alert condition associated with heart failure or a reset threshold indicative of an end of the physiological alert condition according to a state of the physiologic data analyzer circuit so that when the onset threshold is displayed the reset threshold is not displayed and vice versa, the displaying comprising:
in a first state, comparing the determined trend to an onset threshold indicative of onset of a physiological alert condition associated with heart failure, and:
while the determined trend is below the onset threshold, displaying the onset threshold; and
when the determined trend exceeds the onset threshold, displaying the reset threshold and transitioning to a second state;
in the second state, comparing the determined trend to the reset threshold, and:
while the determined trend is above the reset threshold, displaying the determined trend and the reset threshold; and
when the determined trend falls below the reset threshold, display the onset threshold and transitioning to the first state.

16. The patient monitoring system of claim 15, wherein the system includes an implantable or wearable device, the implantable or wearable device including the physiologic data analyzer circuit.

17. The patient monitoring system of claim 16, including a memory circuit, wherein the physiologic data analyzer circuit is configured to store a duration of a physiological alert condition in the memory circuit to be available for review by an external device such as a programmer.

18. The patient monitoring system of claim 15, wherein the physiologic data analyzer circuit is further configured to:
determine a dynamic threshold that varies based on time or a physiologic parameter determined using the physiological information; and
set one of the onset threshold and the reset threshold to the determined dynamic threshold.

19. The patient monitoring system of claim 15, wherein the patient monitoring system comprises an wearable device, and further comprising an external device communicatively coupled to the wearable device, wherein the wearable medical is configured to communicate a beginning and end of an alert period to the external device determined according to the comparing the determined trend to the onset threshold and the reset threshold.

20. The patient monitoring system of claim 19, wherein the external device comprises the display, and wherein the display is configured to show either the onset threshold or the reset threshold as the active threshold for comparing values of the determined trend.

* * * * *